United States Patent [19]
Arnold et al.

[11] 4,108,926
[45] Aug. 22, 1978

[54] REACTIVE PLASTICIZER FOR THERMOPLASTIC POLYSULFONE RESINS

[75] Inventors: Fred E. Arnold, Centerville; Gerard A. Loughran, Kettering, both of Ohio; Anthony Wereta, Jr., Sunny Vale, Calif.

[73] Assignee: The United States of America as represented by the Secretary of the Air Force, Washington, D.C.

[21] Appl. No.: 736,287

[22] Filed: Oct. 28, 1976

[51] Int. Cl.$^2$ .............. C08L 29/10; C08L 49/00; C08L 51/08; C08L 81/06
[52] U.S. Cl. .............. 260/874; 260/30.8 R; 260/607 AR; 528/174; 526/285
[58] Field of Search .............. 260/874, 30.8 R

[56] References Cited
U.S. PATENT DOCUMENTS

4,022,746  5/1977  Kovar et al. .............. 260/874

*Primary Examiner*—Harold D. Anderson
*Attorney, Agent, or Firm*—Joseph E. Rusz; Cedric H. Kuhn

[57] ABSTRACT

The new composition 4,4'-bis(3-ethynylphenoxy)diphenylsulfone is prepared by the nucleophilic displacement reaction of m-hydroxyphenyl acetylene with various disubstituted diphenylsulfones. The composition is useful as a composite resin and also as a reactive plasticizer for polysulfone thermoplastic resins. A reactive plasticizer is a material that remains fluid and acts as a plasticizer during early stages of fabrication and then polymerizes to a rigid resin.

3 Claims, No Drawings

REACTIVE PLASTICIZER FOR THERMOPLASTIC POLYSULFONE RESINS

RIGHTS OF THE GOVERNMENT

The invention described herein may be manufactured and used by or for the Government of the United States for all governmental purposes without the payment of any royalty.

FIELD OF THE INVENTION

This invention relates to 4,4'-bis(3-ethynylphenoxy)-diphenylsulfone. In one aspect it relates to a method for synthesizing the diphenylsulfone. In another aspect it relates to a thermoplastic polymer composition.

BACKGROUND OF THE INVENTION

In recent years there has been an increase in interest in the utilization of thermoplastic resins to reduce the processing cost of fiber-reinforced composites. Thermoplastic matrices offer the possibility of lessening the fabrication costs of advanced structures, thereby making them cost competitive. The cost reductions are possible because faster and less expensive manufacturing procedures can be employed.

Since thermoplastic resins must be processed in the melt under conditions where considerable flow is required, processing temperatures must, unfortunately, be substantially higher than ultimate use temperatures. This limitation presents a serious problem when the thermoplastic resins are considered for use in higher temperature environments. Reactive plasticizers provide a promising solution to this problem.

Reactive plasticizers lower the effective softening point of the thermoplastic resin during processing and then, during a final curing step, they react to form a crosslinked resin. Raising the softening temperature of the mixture to a temperature above the softening point of the neat thermoplastic can result if the molecular structure of the system is appropriately tailored.

It is an object of the present invention, therefore, to provide an improved reactive plasticizer for use in the fabrication of thermoplastic resin composites.

Another object of the invention is to provide a reactive plasticizer for thermoplastic polysulfone resins.

A further object of the invention is to provide a bis-ethynyl aromatic sulfone composition.

Still another object of the invention is to provide a method for synthesizing 4,4'-bis(3-ethynylphenoxy)-diphenylsulfone.

Other objects and advantages of the invention will become apparent to those skilled in the art upon consideration of the ensuing disclosure.

SUMMARY OF THE INVENTION

The present invention resides in a bis-ethynyl aromatic sulfone compound, namely, 4,4'-bis(3-ethynylphenoxy)diphenylsulfone, which has the following formula:

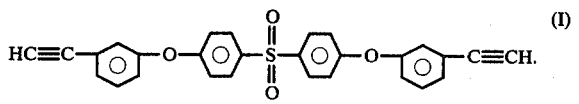

(I)

The diphenyl sulfone compound of this invention is prepared by the nucleophilic displacement reaction of various leaving groups in the 4,4' positions of diphenyl sulfone with the metallic salt of m-hydroxyphenylacetylene. The reaction involved can be represented by the following formula:

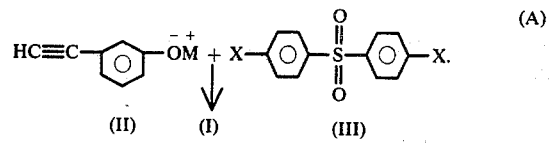

In the foregoing equation (A), M is an alkali metal, e.g., potassium, sodium or lithium, and X is chlorine, bromine, iodine, fluorine or nitro radical. The metallic salt of m-hydroxyphenylacetylene (II) is generated from the base hydrolyses of 3-ethynylphenyl-p-toluene-sulfonate as shown by the following equation:

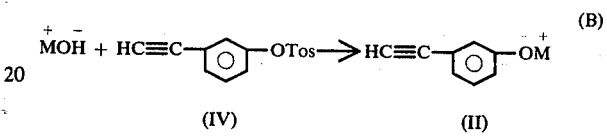

The preparation of 3-ethynylphenyl-p-toluenesulfonate (IV), the precursor for the metallic salt, is described hereinafter in Example I and in U.S. Pat. No. 3,975,444 of common assignee. This patent issued to one of us as a coinventor on Aug. 17, 1976, and its disclosure is incorporated herein by reference.

The reaction illustrated by equation (A) is conducted in an inert atmosphere, employing an aprotic solvent as the reaction medium. Examples of inert gases that can be used include nitrogen, argon, helium, and the like. Examples of suitable aprotic solvents include dimethylacetamide, dimethylsulfoxide, dimethylformamide, hexamethylphosphoramide, and the like. While equimolar amounts of the reactants can be used, it is usually preferred to use an excess of the metal salt, e.g., 1.1 to 3.0 moles of metal salt per mole of the diphenylsulfone. The reaction is usually conducted at a temperature ranging from about 50° to 100° C for a period of about 24 to 120 hours. At the end of the reaction period, the solvent can be conveniently removed by vacuum distillation after which the product is purified, e.g., by column chromatography. In a preferred procedure, the metallic salt of m-hydroxyphenylacetylene (II) is prepared in situ in accordance with equation (B). Thus, 3-ethynylphenyl-p-toluenesulfonate and an excess of the base are refluxed for about 2 to 6 hours in methanol. Benzene is then added to remove water generated as an azeotrope. Thereafter, the methanol is distilled from the reaction mixture and the benzene solution is freeze dried. The freeze dried metallic salt is then reacted with the diphenylsulfone as discussed above.

The diphenylsulfone compound of this invention is particularly useful as a plasticizer for polyphenylenesulfone thermoplastics having the following general formula:

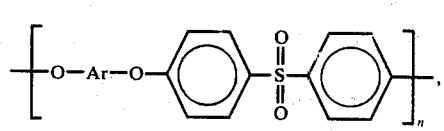

wherein Ar is a divalent aromatic radical and $n$ is an integer corresponding to the number of recurring units. The value of $n$ can vary within a rather broad range, e.g., from about 10 to 200 as determined by the light scattering technique. The number of recurring units (n) can also be defined as such that the polymers have an inherent viscosity of about 0.1 to 1.0 dl/g in dioxane at 30° C. Examples of divalent aromatic radicals include the following:

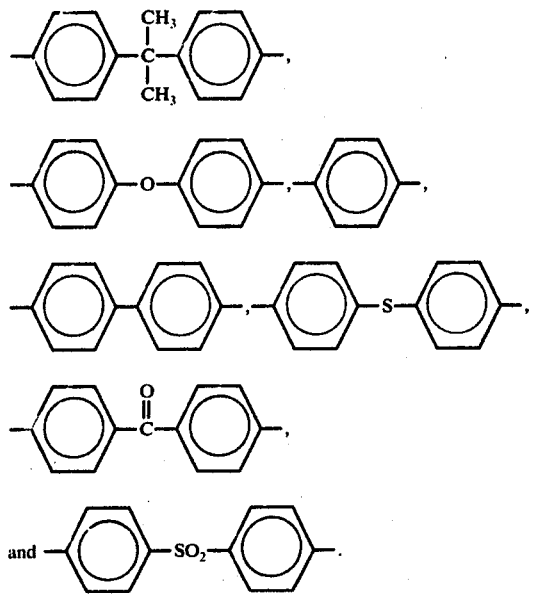

The polyphenylenesulfones are well known polymers that are described in the literature. They can be readily prepared by the solution condensation of a dialkali metal salt of a dihydric phenol with a dihalo aromatic diphenylsulfone in an anhydrous dipolar aprotic solvent at elevated temperatures. The amount of the plasticizer used with the polymer is usually a minor amount, e.g., from about 5 to 30 weight percent, based upon the weight of the polymer.

The diphenylsulfone compound of this invention is also useful as a high temperature matrix resin, utilizing well known processing methods (350° F cure, 500° F postcure). Because of its low glass transition temperature (Tg) the material exhibits excellent tack and drape. Isothermal aging in air of the cured resin shows only a 2 percent weight loss after 300 hours at 500° F and a 22 percent weight loss after 200 hours at 600° F. The material, as a neat resin (film form), fabricated by melt techniques, exhibits a tensile strength of 9,200 psi with a modulus of 450,000 psi after a 4 hour cure at 350° F and a 16 hour postcure at 500° F.

A more complete understanding of the invention can be obtained by referring to the following illustrative examples which are not intended, however, to be unduly limitative of the invention.

EXAMPLE I

Preparation of Precursor
3-ethynylphenyl-p-toluenesulfonate a. α-Chlorocinnamaldehyde-3-yl-(p-toluenesulfonate)

A 5-liter 4-necked round-bottomed flask equipped with stirrer, thermometer, nitrogen inlet adapter and equilibrated addition funnel was thoroughly flamed and purged with nitrogen. Then, 1000 ml of dry, Spectraanalyzed Grade N,N'-dimethylformamide was added and the flask cooled to 20° C. Phosphorus oxychloride (POCl$_3$) was added dropwise (310 g - 2.0 moles) under nitrogen with rapid stirring (exothermic) while maintaining the temperature between 20°-25° C. After completion of the addition, cooling was discontinued and the solution was stirred at room temperature for 1 hour. At this point the solution in the flask was dark red in color. To the reaction flask was rapidly added 300 g (1.03 mole) of dry, solid 3-acetylphenyl(p-toluenesulfonate), and the solution was stirred under nitrogen at 60° C for 3 hours. The dark yellow reaction mixture was then poured into a 4 liter beaker containing 2 liters of ice cold distilled water producing a clear, dark solution. Solid sodium bicarbonate was slowly added to the rapidly stirred solution until foaming ceased and a solid yellow precipitate had formed. Additional ice was added to complete precipitation of the product, and the suspension was stirred for 2 hours. The crude product was filtered by suction, washed with several portions of water, and air-dried. The crude α-chlorocinnamaldehyde-3-yl-(p-toluenesulfonate) thus isolated was used without further purification for the next step, the preparation of 3-ethynylphenyl(p-toluenesulfonate).

A pure sample can be obtained by chromatography of the crude material on a dry column of silica gel, eluting with 2:1 hexane: methylene chloride.

Analysis Calc'd for $C_{16}H_{13}SO_4Cl$: C,57.05; H,3.88. Found: C,56.95; H,3.78.

b. 3-ethynylphenyl-p-toluenesulfonate

To a 5-liter, round-bottomed flask equipped with stirrer, condenser, thermometer and powder funnel, was added 29.5 g (0.74 mole) of solid sodium hydroxide, 1500 ml of water and 1000 ml of p-dioxane. The rapidly stirred mixture was heated to 80° C at which time 125 g (0.37 mole) of α-chlorocinnamaldehyde-3-yl-(p-toluenesulfonate) was added at once through the powder funnel, the funnel being rinsed with p-dioxane. The resulting mixture was stirred at 80° C for 15 minutes, at which time the flask was cooled in ice to room temperature. The contents of the flask were then transferred to a large separatory funnel, and extracted with three 300 ml portions of methylene chloride. Analysis of the extract by TLC (Sio$_2$ strip with UV indicator; eluted with 2:1 hexane:CH$_2$Cl$_2$) showed the product as a dark spot of higher R$_f$ than starting material when viewed under shortwave UV light. The combined methylene chloride extracts were washed with two 100 ml portions of 1N sulfuric acid, and then with two 100 ml portions of water. The organic layer was then separated, and evaporated to dryness in vacuo below 90° C, yielding a dark oil of crude product. This material was triturated with ice water until solidification occurred. The solid product was filtered and air-dried. The dry solid was pulverized to a fine powder which was placed on top of a 2 × 12 inch quartz column of dry silica gel (with UV indicator), forming a broad band. This band was packed down by tapping, and was topped off by an extra inch of silica. The column was now eluted using 2:1 hexane:methylene chloride, a broad band of the desired material removed (as evidenced by complete removal of the dark zone). Evaporation of the eluate in vacuo yielded 75 g (76% yield) of 3-ethynylphenyl(p-toluenesulfonate) as a colorless oil which solidified on cooling into white crystals, m.p., 69°-70° C.

Analysis Calc'd for $C_{15}H_{12}SO_3$: C,66.18; H,4.44. Found: C,66.05; H,4.53.

EXAMPLE II

Preparation of 4,4'-bis(3-ethynylphenoxy)diphenylsulfone from 4,4'-dichlorodiphenylsulfone The potassium salt of m-hydroxyphenylacetylene was prepared by reaction of 98 g (0.36 mole) of 3-ethynylphenyl-p-toluenesulfonate with 47.5 g (0.72 eq) of potassium hydroxide in methanol. The reaction mixture was refluxed for 4 hours and 400 ml of benzene was added to remove the water of hydrolysis as an azeotrope. The methanol was distilled from the reaction mixture and the benzene solution was frozen and freeze dried. To the freeze dried salt was added 34.5 g (0.12 mole) of 4,4'-dichlorodiphenylsulfone and 600 ml of dry dimethylsulfoxide. The reaction mixture was heated at 80° C for 120 hours under nitrogen. The solvent was stripped off under reduced pressure using a rotary evaporator and the residue was purified by column chromatography using silica gel. Elution of the column with a mixture of two parts hexane to one part methylene chloride provided 23.4 g (43% yield) of a light yellow wax, Tg of 14° C. The structure of the compound was confirmed by its infrared spectra, nuclear magnetic resonance spectrum, mass spectrum (m+), 450, and elemental analysis.

Analysis Calc'd for $C_{28}H_{18}O_4S$: C,76.65; H,4.03; S,7.12. Found: C,74.67; H,3.78; S,7.16.

EXAMPLE III

Preparation of 4,4'-bis(3-ethynylphenoxy)diphenylsulfone from 4,4'-difluorodiphenylsulfone To a solution containing 4.9 g (0.018 mole) of 3-ethynylphenyl-p-toluenesulfonate in 100 ml of methanol was added 2.37 g (0.036 eq) of potassium hydroxide. The reaction mixture was refluxed under nitrogen for four hours and 500 ml of benzene was added to remove the water generated as an azeotrope. The methanol was distilled from the reaction mixture and the benzene solution freeze dried. To the freeze dried salt was added 1.53 g (0.006 mole) of 4,4'-difluorodiphenylsulfone dissolved in 75 ml of dry dimethylsulfoxide. The clear brown solution was heated under nitrogen at 75° C, for 120 hours. The dimethylsulfoxide was removed under reduced pressure leaving 5.2 g of an oily residue. The material was purified by column chromatography using silica gel and eluting with a mixture of two parts hexane and one part methylene chloride. Evaporation of the solvents provided 1.7 g (63% yield) of pure product as a light yellow wax, Tg of 14° C.

Analysis Calc'd for $C_{28}H_{18}O_4S$: C,74.65; H,4.03. Found: C,74.25; H,3.93.

EXAMPLE IV

Preparation of 4,4'-bis(3-ethynylphenoxy)diphenylsulfone from 4,4'-dinitrodiphenylsulfone To a solution containing 6.0 g (0.022 mole) of 3-ethynylphenyl-p-toluenesulfonate in 50 ml of methanol was added 2.9 g (0.044 eq) of potassium hydroxide. After refluxing the solution for 3 hours, 500 ml of benzene was added to remove the water of hydrolysis azeotropically. The methanol was distilled from the reaction mixture and the benzene solution was freeze dried. To the freeze dried salt was added 3.5 g (0.009 mole) of 4,4'-dinitrodiphenylsulfone in 150 ml of dry dimethylacetamide. The reaction mixture was heated at 80° C for 48 hours under a nitrogen atmosphere. The dimethylacetamide was removed under reduced pressure and the residual oil purified by column chromatography using silica gel. Elution of the column with a mixture of two parts hexane and one part methylene chloride provided 0.97 g (24% yield) of a yellow wax which had a Tg of 14° C.

Analysis Calc'd for $C_{28}H_{18}O_4S$: C,74.65; H,4.03. Found: C,74.55; H,14.15.

EXAMPLE V

Samples of the reactive plasticizer prepared in Example III were mixed in various percentages with a polysulfone thermoplastic as described hereinbefore. This well known commercially available, thermoplastic polymer is prepared by solution condensation of a dialkali metal salt of bisphenol A with 4,4'-dichlorodiphenylsulfone and exhibited a glass transition temperature (Tg) of 187° C. Various amounts of plasticizer and thermoplastic were dissolved in dioxane and coprecipitated into water. Small samples of the various mixtures were placed in test tubes. The tubes were heated at 550° F for 1 hour, removed and allowed to cool to room temperature. Thermal mechanical analysis (TMA) was determined on the non-cured and cured mixtures to determine the reduction in Tg or the effective lowering of the Tg for fabrication. The data obtained are shown below in Table I.

| % Thermoplastic | % Plasticizer | Tg° C[1] Uncured | Tg° C[1] Cured[3] | Reduction[2] Tg° C |
|---|---|---|---|---|
| 0 | 100 | 14 | | |
| 100 | 0 | 187 | | |
| 90 | 10 | 130 | 190 | 57 |
| 80 | 20 | 100 | 188 | 87 |
| 70 | 30 | 67 | 190 | 120 |

[1]Determined by TMA at a heating rate of 20° C/min.
[2]Reduction in Tg of thermoplastic resulting from plasticizer addition.
[3]Mixture cured at 550° F for one hour.

EXAMPLE VI

The diphenylsulfone compound of this invention, a semisolid material prepared as described in the preceding examples, was used in fabricating graphite reinforced laminates. The prepreg was prepared by hot melt impregnation of AS graphite fibers with the compound. Hot melt temperatures used were in the 100° to 175° F range with best results being achieved at 150° F. The material produced prepreg with excellent room temperature tack and drape. Laminates were fabricated by compressing prepreg plies at 350° F for 2 hours under a pressure of 200 psi and then postcuring in a circulating air oven at 400° to 550° F for four hours. Room temperature short beam shear strengths of the laminates were 8000 to 9000 psi with 100 percent retention of shear strength at 350° F.

The foregoing data demonstrate that 4,4'-bis(3-ethynylphenoxy)diphenylsulfone is an effective reactive plasticizer for polysulfone thermoplastic resins. Thus, the plasticizer lowers the glass transition temperature of the thermoplastic, thereby allowing the polymer to be fabricated at a much lower temperature. The plasticizer then becomes deactivated by addition reaction with itself, which allows the material to be utilized for high temperature applications. The data also show that the diphenylsulfone compound is useful as a high temperature matrix resin.

As will be evident to those skilled in the art, modifications of the present invention can be made in view of the foregoing disclosure without departing from the spirit and scope of the invention.

We claim:

1. A composition consisting essentially of a polyphenylsulfone thermoplastic having repeating units of the formula

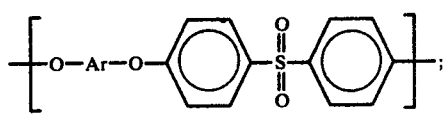

wherein Ar is a divalent aromatic radical; and a plasticizing amount of 4,4'-bis(3-ethynylphenoxy)diphenylsulfone.

2. The composition of claim 1 which consists essentially of the thermoplastic and about 5 to 30 weight percent of 4,4'-bis(3-ethynylphenoxy)diphenylsulfone, based upon the weight of the thermoplastic.

3. The composition of claim 2 in which Ar is a radical selected from the group consisting of

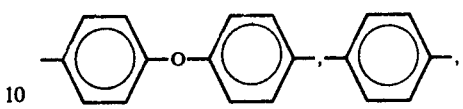

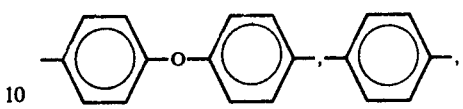

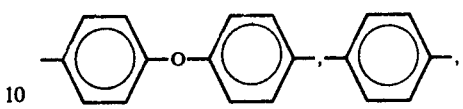

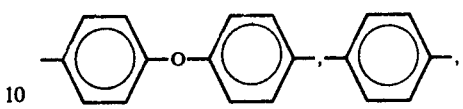

and 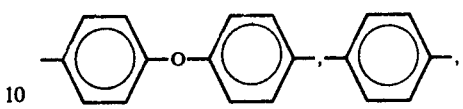

* * * * *